United States Patent [19]

Koulin et al.

[11] Patent Number: 4,977,087

[45] Date of Patent: Dec. 11, 1990

[54] METHOD OF REGENERATING PLANTLETS FROM MESOPHYLL PROTOPLASTS OF PHASEOLUS ANGULARIS

[75] Inventors: Ge Koulin; Wang Yunzhu; Yuan Xunmei; Huang Peiming, all of Shanghai, China

[73] Assignee: Interferon Sciences, Inc., New Brunswick, N.J.

[21] Appl. No.: 145,851

[22] Filed: Jan. 19, 1988

[51] Int. Cl.[5] .......................... C12N 5/02; C12N 5/00
[52] U.S. Cl. ...................... 435/240.47; 435/240.49; 435/240.51; 435/240.54
[58] Field of Search ...................... 435/240.47, 240.49, 435/240.51, 240.54

[56] References Cited

PUBLICATIONS

Crepy et al., 1986, Plant Cell Reports 5(2): 124–126.
Pelcher et al., 1974, Plant Science Letters 3(2): 107–111.
Xu et al., 1981, Z. Pfanzenphysiol, 104(4): 289–298.

Primary Examiner—Elizabeth C. Weimar
Assistant Examiner—David T. Fox
Attorney, Agent, or Firm—Irene J. Frangos

[57] ABSTRACT

A method for regenerating plantlets from protoplasts isolated from mesophyll cells of abacterial seedlings of red bean (*Phaseolus angularis*). Protoplasts cultured in certain liquid media could divide continuously and many protoplast-derived calli may be obtained. In addition, various growth media containing the optimum concentration and the type of sugar, mineral salts, vitamins, and combinations and concentrations of several phytohormones for protoplast growth, division, callus formation and plantlet regeneration are provided.

4 Claims, No Drawings

METHOD OF REGENERATING PLANTLETS FROM MESOPHYLL PROTOPLASTS OF PHASEOLUS ANGULARIS

TECHNICAL FIELD OF THE INVENTION

This invention relates to a method for regenerating plantlets from protoplasts of *Phaseolus angularis*. More particularly, it relates to the regeneration of protoplasts from seedling leaflets of *P. angularis* cells in novel culture media.

BACKGROUND OF THE INVENTION

Leguminous plant tissue culture was first developed by L. G. Nickell [*PNAS* (USA), 42, pp. 848–50 1956)]. Sixteen years later, protoplast culture in leguminous plants was developed [O. L. Camborg et al., *Physiol. Plant*, 30, pp. 125–28 (1974)]. The first successful plantlet regeneration from mesophyll protoplasts was reported in *Medicago sativa* by [K. N. Kao, *Z. Pflanzenphysiol.*, 96, pp. 135–41 (1980)].

Because of its economic importance, plant research relating to legumes has become the focus of many researchers. Means for introducing new genes into protoplasts and cells of various plants are becoming available [See, for example, J. Paszkowski et al., *EMBO Journal*, 3, pp. 2717–2722 (1984); M. Fromm et al., *PNAS* (USA), 82, pp. 5824–28 (1985); J. M. Jaynes et al., Tibtech, pp. 314–20 (1986)]. The transfer of genes can play an important role in improving crops, including legumes by introducing, for example, traits which improve resistance to disease, insects or environmental stress [R.M. Goodman et al., *Science*, 236, pp. 48–54 (1987)].

The process of plantlet regeneration through protoplast culture is time consuming. And the maintenance of a high differentiation capability of calli after a long period of subculturing is the most important factor to plantlet regeneration from protoplast culture. Researchers have found that in the tissue cultures of Indica rice, certain concentrations of 2,4-D, adding Kinetin can effectively promot the formation of embryo-like structure [D. H. Ling, *Acta Botanica Sinica*, 29, pp. 1–8 (1987)].

Unfortunately, the procedure of protoplast culture for leguminous plants is not well established and is so time consuming, that the regeneration of plantlets from protoplasts has been achieved in only a small number of legume species: *Lotus corniculatus, Onobrvchis viciae, Trifolium repens, Vigna aconitifolia, Trigonella corn, Medicago glutinosa, Coronilla varia* [See P. S. Ahuja et al., *Plant Cell Rew.*, 2, pp. 101–04 (1983); P. S. Ahuja et al., *Plant Cell Rew.*, 2, pp. 269–72 (1983); D. Y. Lu et al., *Z. Pflanzenphysiol.*, 107, pp. 59–63 (1982); S. Eapen and R. Gill, *Theor. Appl. Genet.*, 72, pp. 384–87 (1986); A. V. Santos et al., *Z. Pflanzenphysiol.*, 109, pp. 227–34 (1983); A. V. Santos et al., *Z. Pflanzenphysiol.*, 99, pp. 261–70 (1980); D. Y. Lu et al., *Chinese Society for Cell Biology*, Abstract 105, (1986)]. These represent a total of only 25 species of 11 genera of forage or wild legumen [Q. Zhang, Plant Physiology Communications, 5, pp. 66–76 (1986)].

To date, there have been no reports on the regeneration of cultivated seeded legume plants from protoplasts. With respect to Phaseolus, calli have been obtained from protoplasts only in three species, i.e., *P. aureus, P. mungo, P. vulgaris* [M. J. Huang et al., Annual Research Reports, (Institute of Genetics, Academic Sinica) 34 (1982); Z. H. Yu et al., *Z. Planzenphysiol.*, 104, pp. 289–98 (1981); L. E. Pelcher et al., Plant Lett, 32, pp. 107–11 (1974)]; but no plantlet formation has ever been successful. In view of the importance of this food crop, a reliable means for regenerating plantlets from protoplasts continues to be needed.

SUMMARY OF THE INVENTION

The present invention provides a reliable means of plantlet regeneration from protoplast derived calli of *Phaseolus angularis*. More particularly, this invention refers to methods of protoplast culture of abacterial leaves of *P. angularis*, for obtaining vigorous calli from which plantlets may be developed. In addition, preferred media for optimum regeneration are also provided.

DETAILED DESCRIPTION OF THE INVENTION

In order that this invention herein described may be more fully understood, the following detailed description is set forth.

In the description the following terms are employed:

BAP —6-benzyl-aminopurine is a plant hormone, of the cytokinin type.

ZEA —Zeatin is a plant hormone of the cytokinin type.

2,4-D —2,4-dichlorphenoxy-acetic acid is a plant hormone of the auxin type.

NAA —2-naphthylacetic acid is a plant hormone of the auxin type.

GA3 —gibberellin is a plant hormone of the auxin type.

IAA —3-indoleacetic acid is a plant hormone.

Cytokinins —are plant hormones. In low concentrations, these organic substances promote elongation of root cells. Cytokines include Kinetin (KT), BAP and ZEA.

Auxins —are plant hormones. In low concentrations, these organic substances promote elongation of plant shoots and control other specific growth effects. Auxins include 3-(3-indolyl)-propionic acid (IPA), abscisic acid (ABA), and 2,4-D, NAA and GA3.

The present invention relates to the use of mesophyll cells for protoplast isolation and culturing in seeded legume crops (*P. angularis*, red beans), to regenerate plantlets. It is known that, plants of different genotypes within the same species, differ in their capacity to regenerate plantlets in tissue culture, *in vitro*. According to the present invention, different varieties of plants can be used and compared, and suspension culture can be established at an early stage of calli production, to enable the selection of the best genotype and culture conditions for protoplast culture. The methods of the present invention may promote the development of embryoid cells and enhances protoplast plating efficiency, and ultimately the frequency of plant regeneration.

In one aspect, the present invention, relates to the regeneration of intact plantlets from protoplasts of *P. angularis* which are cultured in a medium comprising high concentrations of the phytohormone 2,4-D. In addition, the preferred medium for protoplast regeneration contains a phytohormone of the cytokine-type, selected from BAP or Zeatin, vitamins, mineral salts, and a sugar, preferably glucose. Optimum conditions for regeneration are provided, including using red light instead of white light for cell differentiation.

In another aspect of the invention, exogenous DNA is introduced into the protoplasts before culturing to form calli. Means for gene transfer include transformation by direct DNA transfer, either by microinjection or DNA uptake, by virally mediated gene transfer, or by a variety of other methods available to those of skill in the art [see for example, R. M. Goodman et al., "Gene Transfer in Crop Improvement", Science, 236, pp. 48–54 (1987)]. Any of a wide variety of means to introduce exogenous DNA into the protoplasts are useful and are envisioned as a within the scope of this invention.

In order that this invention may be better understood, the following example is set forth. This example is for purposes of illustration only and is not to be construed as limiting the scope of the invention.

EXAMPLE

PREPARATION OF SEEDLINGS

We rinsed red beans seeds in 70%(v/v) alcohol for 2 minutes, surface sterilized them for 20 min. with 0.1% $HgCl_2$ and washed them with sterilized distilled water. We then inoculated in M. S. solid medium with 1 mg/l ZT, 20% sugar and placed them in a culture room at 25° to 27° C., 1500 Lux daylight for 12 hrs.

Isolation of Protoplasts

After the seeds had germinated for 11 to 16 days, we harvested 16 first leaves and cut them into pieces of about 1 to 2 $mm^2$. These pieces of leaves were immersed in 5 ml 13% CPW 13M enzyme solution consisting of 0.7% (w/v) cellulase ("ONOZUKA" R-10, Yakult Pharmaceutical Industry Co., Ltd., Japan), 0.7% hemicellulase (No. H-2125, Sigma Chemical Company, USA), pH 5.8 [E. M. Frearson et al., Devel. Biol., 35, pp. 130–37 (1973)]. After shaking the mixture (50 rpm, 25° to 27° C.) for 14 hours, we filtered the enzyme solution through a 50 μm stainless steel mesh (50u poresize), and collected the protoplasts by centrifugation (500 rpm) for 2 minutes.

We washed the protoplasts with CPW13M solution three times. We resuspended the protoplasts in a liquid culture medium with a final density of about $5 \times 10^5$ to $1 \times 10^6$/ml. We added 1 ml of the protoplast suspension/solution into a culture bottle (60×30×20 mm) and cultured in an artificial weather chamber at 26.5° to 27.5° C., 200 Lux daylight for 24 hr. The components of protoplast culture media are shown below in Table 1:

TABLE 1

| COMPOSITION OF MEDIA FOR PROTOPLAST CULTURE (mg/l) | | | | | |
|---|---|---|---|---|---|
| | I-1 | I-2 | I-3 | I-4 | III-S-2 |
| MACRO-ELEMENTS | MS* | MS* | $D_{2a}$** | $D_{2a}$ | $D_{2a}$ |
| MICRO-ELEMENTS | MS | MS | MS | MS | MS |
| VITAMINS | MS | $D_{2a}$ | $D_{2a}$ | $D_{2a}$ | $D_{2a}$ |
| SUGAR | | | | | |
| GLUCOSE | 30000 | 30000 | 30000 | 30000 | 5000 |
| MANNITOL | 45000 | 45000 | 45000 | 45000 | 0 |
| SUCROSE | 30000 | 30000 | 30000 | 30000 | 30000 |
| HORMONE | | | | | |
| 2,4-D | 0.5 | 0.5 | 0.5 | 0.5 | 3 |
| NAA | 0.5 | 0.5 | 0.5 | 0.5 | 0 |
| 6BA | 0.5 | 0.5 | 0.5 | 0.5 | 0.2 |
| ZEATIN | 0.5 | 0.5 | 0.5 | 0.5 | 0 |
| LACTALBUMIN HYDROLYSATE | 500 | 500 | 500 | 500 | 500 |
| AMINO ACIDS | | | | | |
| ARGININE | 0 | 0 | 0 | 10 | 0 |
| GLUTAMINE | 0 | 0 | 0 | 292.3 | 0 |
| AGAR | 0 | 0 | 0 | 0 | 5000 |

MS*; the same as MS except the concentration of $CaCl_2$ was enhanced to 900 mg/l.
**X.H. Li, Theor. Appl. Genet., 60, pp. 345–47 (1981)

TABLE 2

| COMPOSITION OF MACROELEMENTS AND VITAMINS | | | | | |
|---|---|---|---|---|---|
| MACRO-ELEMENTS | MS* | $D_{2a}$ | VITAMIN | MS | $D_{2a}$ |
| $CaCl_2 2H_2O$ | 900 | 900 | Biotin | 0 | 0.04 |
| $KNO_3$ | 1900 | 1480 | Folic Acid | 0 | 0.4 |
| $NH_4NO_3$ | 1650 | 270 | Inositol | 100 | 100 |
| $KH_2PO_4$ | 170 | 80 | Thiamin-HCl | 0.4 | 4.0 |
| $MgSO_4 7H_2O$ | 370 | 900 | Pyridoxine-HCl | 0.5 | 0.7 |
| | | | Glycine | 2 | 1.4 |
| | | | Nicotinic Acid | 0.5 | 4.0 |

During the protoplast culture, the regenerated cells grew differently in association with different culture media. When cultured in suitable media, the round protoplasts of the red bean began to expand and became elliptical in shape. After 4 days, the regenerated cells began their first division and 3 days later, the second division began. Alternatively, when regenerated cells were cultured in unsuitable media, they contracted and disintegrated or substantially decreased in the amount of cytoplasm. We calculated plating efficiency after culturing for 8 days, as follows:

$$\text{Plating efficiency} = \frac{\text{No. of dividing cells}}{\text{No. of calculated cells}}$$

We counted 500 cells during each of three treatments. After culturing for about 30 days, many calli formed.

We observed that one of the important factos in protoplast culture is the selection of the suitable concentration and type of sugar. Using I-3 medium (Table 1) we tested different concentrations of sucrose, glucose and mannitol for determining the optimum type and concentration of sugar source. Our results are listed in Table 3.

TABLE 3

| Name of Media | G | M | S | C | Cell Growth Status | Plating Efficiency |
|---|---|---|---|---|---|---|
| | (Molarity) | | | | | |
| I-3-GO.8 | 0.8 | 0 | 0 | 0.8 | +++ | 0 |
| I-3-GO.7 | 0.7 | 0 | 0 | 0.7 | +++ | 0.3 |
| I-3-GO.6 | 0.6 | 0 | 0 | 0.6 | ++++ | 5.5 |
| I-3-GO.5 | 0.5 | 0 | 0 | 0.5 | ++++ | 2.9 |
| I-3-GO.4 | 0.4 | 0 | 0 | 0.4 | + | 0 |
| I-3-GO.3 | 0.3 | 0 | 0 | 0.3 | ± | 0 |
| I-3-MSO.6 | 0 | 0.5 | 0.1 | 0.6 | +++ | 0.1 |
| I-3-MSO.5 | 0 | 0.4 | 0.1 | 0.5 | ++ | 0 |
| I-3-MSGO.6 | 0.15 | 0.35 | 0.1 | 0.6 | +++ | 0.7 |
| I-3-MSGO.5 | 0.15 | 0.25 | 0.1 | 0.5 | + | 0 |
| I-3-MSGO.4 | 0.15 | 0.15 | 0.1 | 0.4 | + | 0 |

++++ = very good; +++ = good; ++ = fair; + = poor; ± = bad.
G = glucose; M = mannitol; S = sucrose; C = final concentration of sugar Among the different kinds of carbon sources we tested, glucose proved to be the most suitable for the growth and division of protoplasts, both as a single carbon source and an osmotic pressure stabilizer. With respect to the concentration of glucose, we tested from 0.3M to 0.8M. Media comprising 0.5M to 0.6M glucose gave rise to the best results in growth and division of protoplasts. When the glucose concentration fell to below 0.5M, the protoplasts usually ceased to grow and the plating efficiency declined to zero. If the glucose concentration rose above 0.6M, few (see Table 3, I-3-G0.7) or no (see Table 3, I-3-G0.8) protoplasts divided after culture for 8 days, but the growth of protoplast was successfully nurtured.

We tested glucose as carbon source and mannitol as osmotic stabilizer, with the total sugar concentration of 0.5M to 0.6M (Table 3, I-3-MS0.5; 0.6), but protoplast growth worsened and few or no divisions could be seen. Using sucrose as carbon source and mannitol as osmotic stabilizer, with various amounts of glucose (Table 3, I-3-MSG0.5; 0.6), plating efficiency in I-3-MSG0.6 was enhanced (compare I-3-MS0.6). was less efficient for cell division (I-3-MSG0.5; I-3-MS0.5). Our results indicated that sucrose and mannitol inhibited the growth and division of protoplast to some extent. Even an adequate supplement of glucose could not counteract this effect. Other studies have been done to ascertain the optimum concentration and type of sugar source for protoplast regeneration, but there is still no consensus of opinion [see *Institute of Plant Physiology*, Cell Research Section: Plant Tissue and Cell Culture, pp. 269–94 (1978); Z. H. Zu et al., *Z.Pflanzenphysiol*, 104, pp. 289–98 (1981); M. J. Huang et al., *supra*].

We also studied the effect of macroelements of mineral salts and vitamins on the division of protoplast in 0.6M glucose media had a different effect on the plating efficiency. The main differences between media I-1 and I-3 in Table 1 was in the concentration and the type of macroelements; the former had higher ammonium nitrate, lower concentration of Mg ion as in $D_2a$ medium and higher a concentration and variety of vitamins as in $D_2a$ medium.

Referring to Table 4, our results indicates (Table 4) that media containing high concentrations of vitamins, Mg ion, and lower concentration of ammonium nitrate enhanced the plating efficiency of protoplasts.

TABLE 4

| INFLUENCE OF THE MACROELEMENTS AND THE VITAMINS ON THE PLATING EFFICIENCY | | |
|---|---|---|
| Name of Media | Growth Status of Cell | Plating Efficiency (%) |
| I-3-GO.6 | ++++ | 5.5 |
| I-1-GO.6 | +++ | 0.8 |

It has been said that ammonium ion has a poisonous effect on protoplasts. As a result, some researchers have reduced or completely deleted the concentration of the ammonium ion in protoplast culture [M. D. Upaothya, *Potato Res.*, 18, pp. 438–45 (1975)]. But in sun flower cultures, using 15mM $KNO_3$ as single nitrogen source was gave poor results for protoplast culture, while the results using lower mineral nitrogen or amino acid was better [P. Lenee and Y. Chupeau, *Plant Science*, 43, pp. 69–75 (1986)]. In rice culture (*Oryza sativa*) protoplast cultures, using an amino acid mixture as a unique nitrogen source also improves the results [K. Toriyama and K. Hinata, *Plant Science*, 41, pp. 179–83 (1985)]. It could be seen from these results that decreasing the amount of mineral nitrogen in medium might improve the growth of the regenerated cells.

We observed that phytohormones possessed a certain effect on the growth and division of protoplasts (Table 5). When four kinds of hormones, i.e., 2,4-D, NAA, BAP, Zeatin, were added in media (all were used in the concentration of 0.5mg/l) the protoplasts grew best. Using two types of hormones, auxin 2,4-D combined with cytokine BAP or Zeatin, the results were better than when we used a single hormone. 2,4-D combined with NAA was worse than 2,4-D used alone for protoplast culture. When the four kinds of hormones were used alone, NAA showed the worst result for the division of protoplast.

TABLE 5

| INFLUENCE OF HORMONES ON THE GROWTH STATUS OF REGENERATED CELLS | | | | | |
|---|---|---|---|---|---|
| Name of Media | 6BA | Zeatin | 2,4-D | NAA | Cell Growth Status |
| | | (mg/l) | | | |
| I-3 | 0.5 | 0.5 | 0.5 | 0.5 | ++ |
| I-3A | 0.5 | 0 | 0 | 0 | + |
| I-3B | 0 | 0.5 | 0 | 0 | + |
| I-3C | 0 | 0 | 0.5 | 0 | + |
| I-3D | 0 | 0 | 0 | 0 | ± |
| I-3E | 0.5 | 0 | 0.5 | 0 | ++ |
| I-3F | 0 | 0.5 | 0.5 | 0 | ++ |
| I-3G | 0 | 0 | 0.5 | 0.5 | ± |

We also found that the growth of protoplasts worsened if arginine and glutamine were added in primary stage of red bean protoplast culture. (Table 1) This result was similar to that seen in green bean (*P. aureus*) [Z. H. Xu et al., *Z. Planzenphysiol.*, 104, pp. 289–98 (1981)].

CALLUS FORMATION

After culturing the protoplasts for 20 days, we observed small calli in the culture bottle. After 30 days, the diameter of the calli reached 1 to 2 millimeters and calli were transferred to solid medium III-s-2 for callus amplification. Ten days later, calli became obviously larger and green pigment appeared in some calli. The results concerning the induction of calli are described in Table 6, below.

TABLE 6

| CALLUS FORMATION FROM PROTOPLASTS DERIVED CELL | | | |
|---|---|---|---|
| Name of Media | Times of Experiments (bottle) | Inoculated Protoplasts Calli | % |
| I-3-GO.8 | 5 | 5 | 0 | 0 |
| I-3-GO.7 | 5 | 5 | 1 | 20 |
| I-3-GO.6 | 9 | 9 | 7 | 75 |
| I-3-GO.5 | 5 | 5 | 3 | 60 |
| I-3-GO.4 | 5 | 5 | 0 | 0 |
| I-3-GO.3 | 5 | 5 | 0 | 0 |
| I-3-MSO.6 | 5 | 5 | 0 | 0 |
| I-3-MSO.5 | 5 | 5 | 0 | 0 |
| I-3-MSGO.6 | 5 | 5 | 1 | 20 |
| I-3-MSGO.5 | 5 | 5 | 0 | 0 |

It must be noted that there is a close relationship between the formation of calli and the growth status or the division of protoplasts. When regenerated cells grew better with high division efficiency, the frequency of callus formation was correspond high. It also indicated that 0.6M glucose as single carbon source and osmotic stabilizer was suitable not only to the growth, division of protoplast, but also formation of the calli.

Plantlet Regeneration

Regenerated calli were usually subcultured once every two weeks. After culturing for about 100 days, the calli were transferred to differentiation media. Our differentiation media consisted of MS supplemented with various combinations of phytohormones, auxins and cytokinins, in various concentrations we observed that high concentrations of 2,4-D (i.e. 3 mg/l of 2,4-D in relation to 0.2mg/l 6BA) amplified calli into embryo-like structures most effectively. We used ordinary fluorescence (wave length 520nm) and long wave fluorescence (wave length 720nm) as illumination (1600 Lux, 14 hr a day, 22 to 26° C.).

The subculture time was then shortened to 7 days, repeatedly. The texture of the calli developed an embryo-like structure and the roots differentiated strongly. Even in the control (hormone-free), the rooting frequency of the calli reached 40%. Calli could propagate to 4 to 5 times in the media containing GA3 and the texture remained granular-like, but the calli failed to differentiate.

If the subculture time of calli was prolonged (to more than three weeks), the moisture content in the callus increased gradually and some formed hairroots, while others turned paste-like. When vigorous calli were frequently subcultured onto differentiation media, adding cytokinin (6BA, 1mg/l) alone or supplemented with lower concentration of auxin (6BA 5 mg/l, NAA0.2mg/l, IAA0.1 mg/l), they would quickly form an embryo-like structure. The surface granules developed and produced special layer structures which looked like bud scales.

After culturing for 96 days, several calli having a diameter of 1 to 1.5 cm (Table 7; treatment 102 and 108), began to form green spots and shoots. On subsequent transfer to ½MS (containing one-half of the ingredients) hormone-free or 1mg/l NAA supplemented media, intact plantlets could develop 7 to 10 days later. Several batches of shoots were obtained from a single differentiating callus.

Table 7 sets forth the influence of hormones on organ differentiation for protoplast regeneration of calli:

TABLE 7

| No. of Treatment | Hormone (mg/l) | | | | No. of Calli Inoculated | No. of Root (%) | Seedling (%) |
| --- | --- | --- | --- | --- | --- | --- | --- |
| | 6BA | NAA | IAA | GA3 | | | |
| 102 | 1 | 0 | 0 | 0 | 12 | 2(17) | 7(58) |
| 103 | 3 | 0 | 0 | 0 | 15 | 0(0) | 0(0) |
| 104 | 5 | 0 | 0 | 0 | 12 | 1(8) | 0(0) |
| | 7 | 0 | 0 | 0 | — | — | — |
| 105 | 10 | 0 | 0 | 0 | 12 | 0(0) | 0(0) |
| 106 | 1 | 0.2 | 0.1 | 0 | 10 | 6(60) | 0(0) |
| 107 | 3 | 0.2 | 0.1 | 0 | 19 | 0(0) | 0(0) |
| 108 | 5 | 0.2 | 0.1 | 0 | 10 | 1(10) | 6(60) |
| 109 | 7 | 0.2 | 0.1 | 0 | 22 | 0(0) | 0(0) |
| 110 | 10 | 0.2 | 0.1 | 0 | 13 | 0(0) | 0(0) |
| 111 | 1 | 0.4 | 0.1 | 0 | 11 | 5(45) | 0(0) |
| 112 | 3 | 0.4 | 0.1 | 0 | 17 | 0(0) | 0(0) |
| 113 | 5 | 0.4 | 0.1 | 0 | 20 | 4(20) | 0(0) |
| 114 | 7 | 0.4 | 0.1 | 0 | 18 | 0(0) | 0(0) |
| 115 | 10 | 0.4 | 0.1 | 0 | 15 | 0(0) | 0(0) |
| 116 | 1 | 0.4 | 0.1 | 0.3 | 9 | 1(11) | 0(0) |
| 117 | 3 | 0.4 | 0.1 | 0.3 | 13 | 0(0) | 0(0) |
| 118 | 5 | 0.4 | 0.1 | 0.3 | 19 | 0(0) | 0(0) |
| 119 | 7 | 0.4 | 0.1 | 0.3 | 17 | 0(0) | 0(0) |
| 120 | 10 | 0.4 | 0.1 | 0.3 | 13 | 0(0) | 0(0) |
| 101 | 0 | 0 | 0 | 0 | 25 | 10(40) | 0(0) |

We used long wave red plant growth light as a light source for cell differentiation. A larger number of plantlets regenerated from protoplasts under the red light than under the white fluorescent light, i.e., the control. However, the embryoid structure under later condition was good, and the seedlings were stronger than under the red light. The results of our analysis of the effect of light of different wave lengths on organ differentiation in protoplast culture, are set forth in Table 8:

TABLE 8

| | White Light (CK) | Red Light |
| --- | --- | --- |
| No. of Calli | 96 | 147 |
| No. of Cali Differentiated into seedling (%) | 1(1) | 6(4) |
| No. of Calli Differentiated into Root (%) | 8(8) | 17(12) |
| Total No. of Seedling (%) | 1(1) | 12(8) |

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim

1. A method of regenerating *Phaseolous angularis* plantlets from protoplasts which comprises obtaining protoplasts from the mesophyll of abacterial seedings of *P. angularis*, culturing the protoplasts so obtained in a suitable protoplast culture medium comprising a 0.5M to 0.6M of glucose, and a mixture of phytohormones comprising 2,4-D and at least one other hormone selected from the group consisting of 6BA, and Zeatin, to produce calli and culturing the calli so produced on a suitable differentiation medium comprising 6BA and at least one other hormone selected from the group consisting of 2,4-D and a mixture of NNA and IAA; differentiating the calli under long wave red light so as to produce *P. angularis* plantlets.

2. The method according to claim 1 wherein the protoplast culture medium also comprises vitamins, and mineral salts.

3. The method of claim 1 wherein the protoplast culture medium further comprises about 900 mg/liter of $MgSO_4 7H_2O$ and about 270 mg/liter of $NH_4NO_3$.

4. A method for regenerating *P. angularis* plantlets from protoplasts comprising;
(a) sterilizing seeds from *P. angularis* with $HgCl_2$ to produce sterilized seeds;
(b) incubating the sterilized seeds for between 11 to 16 days on MS solid medium supplemented with 1mg/l ZT, and 20% sugar in light at 25°-27° C., to cause the seeds to germinate;
(c) harvesting leaves from the germinated seeds and cutting them;
(d) immersing the cut leaves in 5 ml 13% enzyme solution, comprising 7% cellulase at pH 5.8;
(e) incubating the mixture prepared according to (d), at 25°-27° C., with slight agitation for 14 hours;
(f) filtering the solution through a 50 um stainless steel mesh after incubation so as to remove debris and cells and then centrifuging the filtrate to sediment protoplasts;
(g) collecting and washing the protoplasts so obtained with a CPW13M solution;
(h) suspending the protoplasts in a protoplast culture medium comprising 0.50 to 0.6M glucose and phytohormones 24-D, NAA, 6BA and Zeatin;
(i) culturing the suspended protoplasts in a thin layer of liquid of the protoplast culture medium at about 27° C. in daylight for about 30 days until they form small calli of about 1 to 2 millimeters;

(j) transferring the calli of 1-2 millimeters in diameter to solid calli expansion medium and subculturing every two weeks for a total of about 100 days;

(k) transferring the calli to differentiation media and subculturing every 7 days, for about 96 days until an embryo-like structure develops;

(l) transferring to hormone-free media, maintaining the embyro-like structures in red light until plantlets are produced; and (m) subculturing using differentiation medium comprising one or more cytokinins and auxins in fluorescent light 14 hours a day at 22°-26° C.

* * * * *